(12) United States Patent
Elhabashy

(10) Patent No.: US 11,612,535 B2
(45) Date of Patent: Mar. 28, 2023

(54) SURGERY PILLOW AND DEVICE COMBINING ENDOTRACHEAL TUBE HOLDER, BITE GUARD, AND PATIENT EYE PROTECTOR

(71) Applicant: Basim Elhabashy, Boca Raton, FL (US)

(72) Inventor: Basim Elhabashy, Boca Raton, FL (US)

(73) Assignee: PYRAMIDS MED LLC, Boca Raton, FL (US)

( * ) Notice: Subject to any disclaimer, the term of this patent is extended or adjusted under 35 U.S.C. 154(b) by 0 days.

(21) Appl. No.: 17/171,362

(22) Filed: Feb. 9, 2021

(65) Prior Publication Data

US 2022/0249310 A1   Aug. 11, 2022

(51) Int. Cl.

| A61G 13/12 | (2006.01) |
|---|---|
| A61M 16/04 | (2006.01) |
| A61M 25/02 | (2006.01) |
| A47G 9/10 | (2006.01) |
| A61F 9/04 | (2006.01) |

(52) U.S. Cl.
CPC .......... *A61G 13/1215* (2013.01); *A47G 9/10* (2013.01); *A61F 9/04* (2013.01); *A61G 13/122* (2013.01); *A61G 13/129* (2013.01); *A61G 13/1255* (2013.01); *A61G 13/1295* (2013.01); *A61M 16/0493* (2014.02); *A61M 16/0497* (2013.01); *A61M 25/02* (2013.01); *A47G 2009/1018* (2013.01); *A61G 2200/325* (2013.01); *A61G 2200/327* (2013.01); *A61M 2025/022* (2013.01); *A61M 2025/026* (2013.01)

(58) Field of Classification Search
CPC ............ A61G 13/1215; A61G 13/1295; A61G 2200/325; A61G 13/121; A61G 7/07; A47G 9/10; A47G 2009/1018; A61F 9/04; A61M 16/0497; A61M 16/0493; A61M 25/02; A61M 2025/022; A61B 1/267
See application file for complete search history.

(56) References Cited

U.S. PATENT DOCUMENTS

| 6,796,310 B2* | 9/2004 | Bierman | A61M 16/0488 128/202.18 |
|---|---|---|---|
| 6,935,340 B2* | 8/2005 | Saied | A61M 16/0488 128/845 |
| 2007/0107130 A1* | 5/2007 | Elhabashy | A61B 50/20 5/622 |

FOREIGN PATENT DOCUMENTS

| WO | WO-9965553 A1 * | 12/1999 | ........ A61M 16/0488 |
|---|---|---|---|
| WO | WO-2016141210 A1 * | 9/2016 | ............... A61F 9/04 |

* cited by examiner

*Primary Examiner* — David R Hare
*Assistant Examiner* — Madison Emanski
(74) *Attorney, Agent, or Firm* — Malloy & Malloy, P.L.; Robert M. Downey

(57) ABSTRACT

A surgery apparatus includes a resilient foam pillow having an arrangement of labeled tabs for holding lines leading to/from a patient during and after surgery. A central cutout area in the pillow accommodates the patient's eyes, nose and mouth when in the prone position. Left and right channels in the foam pillow extend from a top edge of the pillow to the central cutout area for holding a breathing tube system. The foam pillow further includes a removably attachable chest support and opposite shoulder supports. A multipurpose holder device for placement on the patient's head has an arrangement of straps for securing an eye shield, a bite block and ventilator tube securing straps on the patient during surgery.

6 Claims, 8 Drawing Sheets

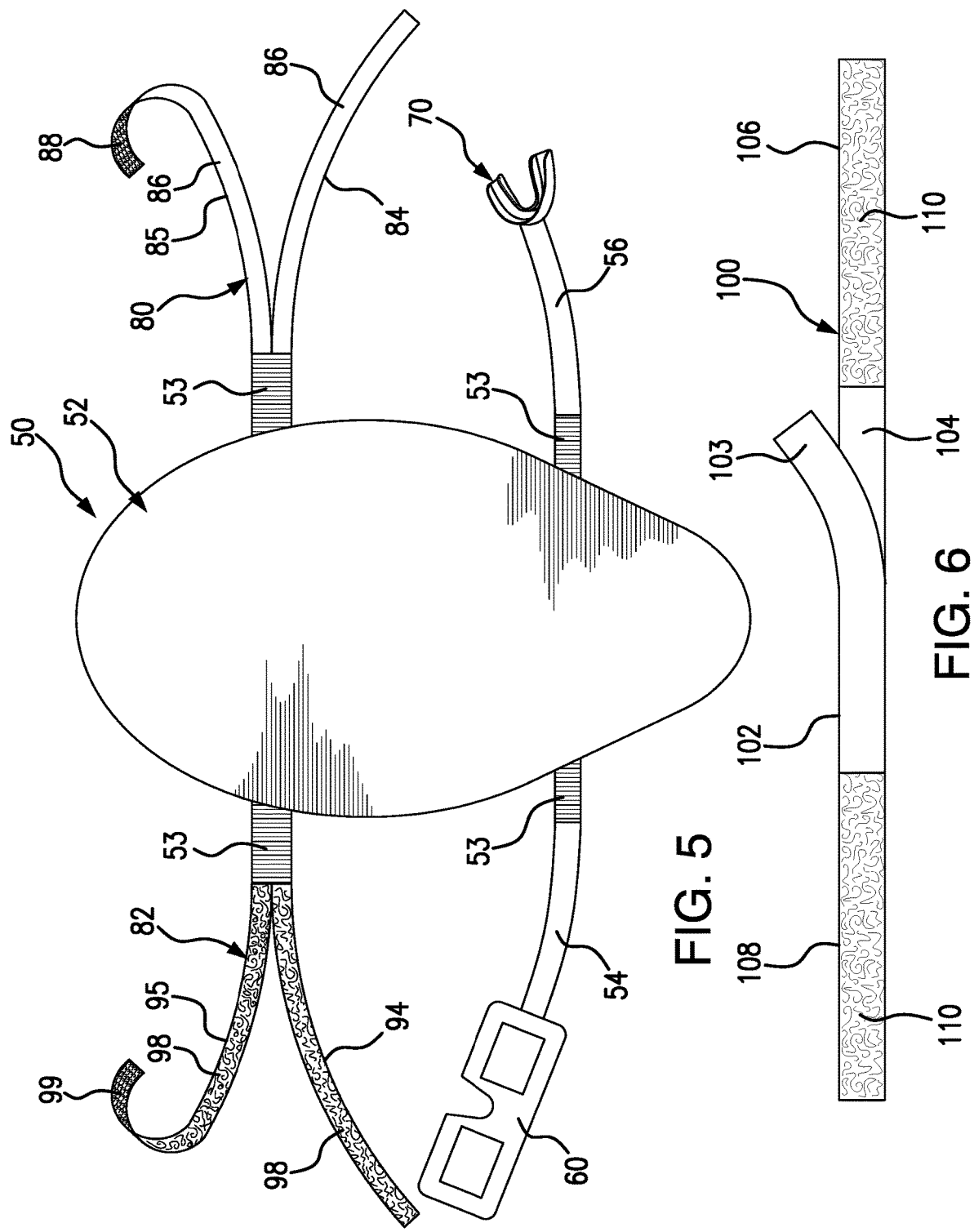

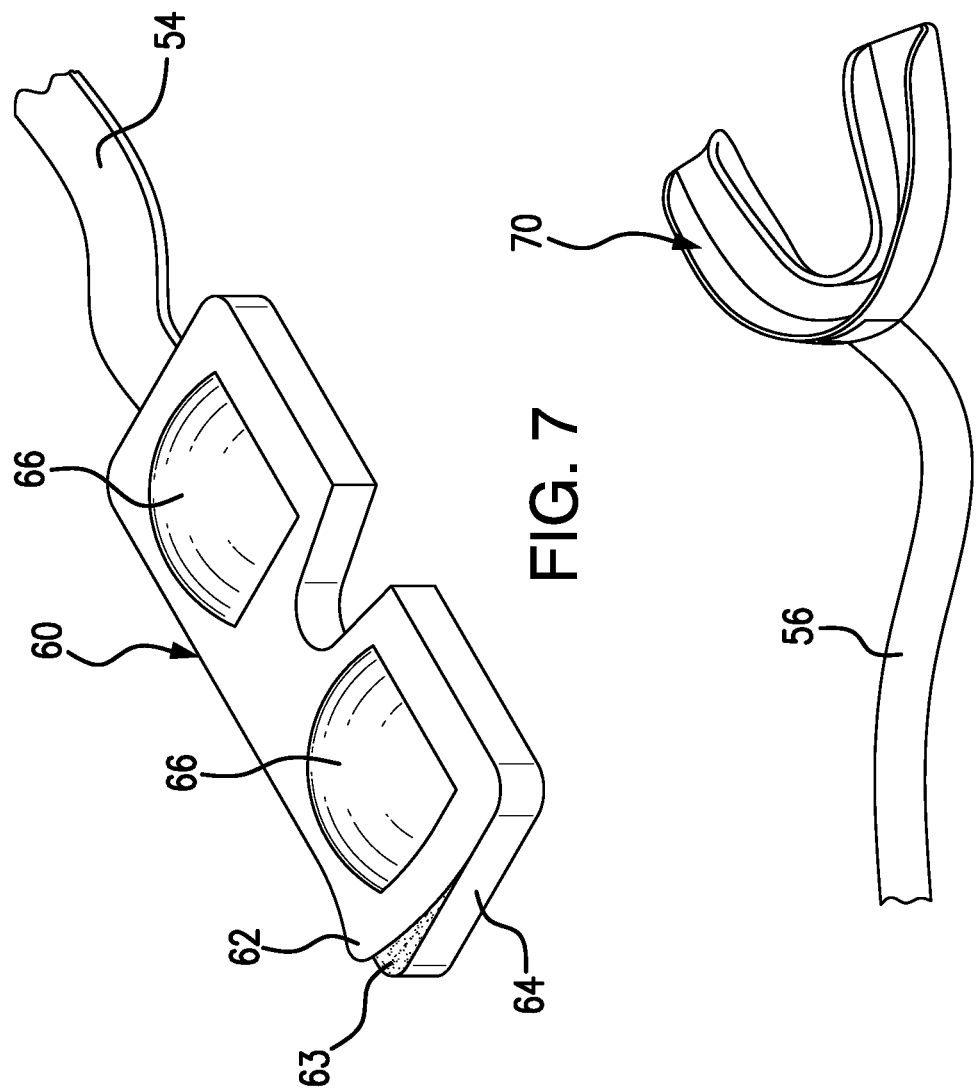

SURGERY PILLOW AND DEVICE COMBINING ENDOTRACHEAL TUBE HOLDER, BITE GUARD, AND PATIENT EYE PROTECTOR

BACKGROUND OF THE INVENTION

Field of the Invention

The present invention relates to a multifunctional surgery apparatus for organizing and maintaining various devices in a readily accessible manner for surgery and, more particularly, to a surgery apparatus including a resilient foam pillow and a multipurpose device for holding an eye shield, bite block and ventilator tube securing straps for convenient and ready use on a patient being prepared for surgery in an operating room.

Description of the Related Art

When a patient arrives at the operating room for surgery, the anesthesiologist will ordinarily attach a host of invasive tubes, lines, catheters, wires and other devices to the patient for use throughout the surgery and afterwards. Additionally, it is often necessary to place a protective eye shield over the patient's eyes, as well as a bite block in the patient's mouth when the patient is intubated with an endotracheal tube. Moreover, depending on the size and anatomy of the patient, and the positioning of the patient on the operating table (i.e., prone position or supine position) it may be necessary to place additional support at various areas of the patient to avoid areas of excessive pressure that might effect blood supply and/or cause nerve damage. For instance, when a patient is in the prone position (i.e., chest down and back facing up) it is sometimes necessary to place a chest roll under the patient's upper chest area. This is particularly necessary for female patients that may have large breasts, in order to elevate the chest so that the patient doesn't experience excessive pressure on the breasts that may negatively impact blood supply. In addition, or alternatively, it may be necessary to place padded supports under the patient's shoulders, particularly when in the prone position, again for the purpose of preventing excessive pressure and/or nerve damage during surgery.

Surgeries that are performed under general anesthesia will require the patient to be intubated with an endotracheal tube that attaches to a breathing tube system and a ventilator. In this instance, it is extremely important to secure the endotracheal tube exiting the patient's mouth so that the endotracheal tube does not become partially or fully dislodged once the patient has been intubated. Typically, to secure the endotracheal tube in place, an adhesive tape is wrapped around the endotracheal tube and secured to the user's face, above and below the lips. However, in the instance that the patient has facial hair, and particularly a mustache, it can be difficult to secure the adhesive tape to the patient because the adhesive does not easily adhere to the facial hair. This can present a dangerous situation because if the endotracheal tube is not adequately secured in place, it could become dislodged during surgery. In this event, the surgery needs to be interrupted and the medical staff needs to perform a new intubation procedure to once again properly intubate the endotracheal tube within the patient.

When preparing for surgery, it is necessary to have all of the needed devices and other items readily available and in place for use on the patient. However, it is very common to have a situation where one or more items may be missing, such as an eye shield, a bite block or a chest roll. In this event, one of the attending medical staff must conduct a search in inventory for the items. Sometimes this is not practical, or the missing item is not in close proximity to the operating room. Obviously, this is an undesirable situation and often the attending medical staff must improvise by doing such things as rolling up towels to create a chest support or shoulder supports, or other innovative techniques in an attempt to replace the missing item such as an eye shield or bite block.

Accordingly, there remains a definite and urgent need in the medical field for a surgery apparatus that allows for convenient and efficient organizing and maintaining of various devices in a readily accessible manner prior to, during and after surgery. More particularly, there remains a need for a device that can be secured to the patient's head and which has an eye shield, bite block and endotracheal tube securing mechanism readily available on the device for fast and efficient use by the attending medical personnel when preparing a patient for surgery in the operating room.

SUMMARY OF THE INVENTION

The present invention relates to a surgery apparatus and, more particularly, to a resilient foam pillow for supporting a patient's head while on an operating table for surgery. In a preferred embodiment, the resilient foam pillow includes an arrangement of labeled tabs for holding lines leading to and from a patient during and after surgery. The labeled tabs hold the various lines, tubes and catheters and help the anesthesiologist organize these different intravenous and arterial lines, catheters, monitoring cables, pressure transducers and other devices coming from or going to the patient. This allows the anesthesiologist and others to quickly locate and identify each particular line, tube, catheter, etc.

A central cutout area in the top of the pillow accommodates the patient's eyes, nose and mouth, particularly when in the prone position so that there is sufficient space between the pillow and the patient's eyes, nose and mouth. This allows for an endotracheal tube to exit the patient's mouth without obstruction by the pillow. It also eliminates unwanted pressure and contact of the pillow against the patient's eyes, nose and mouth while the patient is under general anesthesia. The pillow includes left and right channels in the top side, leading from a top edge of the pillow and to the central cutout area. Depending on the positioning of the patient and the desired placement of the endotracheal tube and breathing tube system, either the left channel or right channel is used for holding the breathing tube system that connects between a ventilator and the endotracheal tube exiting the patient's mouth. The pillow further includes a removably attachable chest support and opposite shoulder supports. The chest support and opposite shoulder supports are constructed of the same resilient foam material as the pillow and are selectively attachable and removable to the bottom edge of the pillow with the use of hook and loop fasteners or other releasable attachment mechanisms. Use of the chest support and opposite shoulder supports will depend upon the patient, as well as the positioning of the patient (i.e., in the prone position, supine position or on their side). Generally, the chest support is primarily used when a patient is in the prone position, wherein the chest support alleviates pressure on the patient's chest, particularly female patients that may have larger sized breasts. The shoulder supports may also be used in combination with the chest support or without the chest support. The opposite shoulder supports are square or rectangular in shape and are placed at the opposite ends of the bottom edge of the pillow or near the opposite ends of the chest support for positioning directly below the patient's shoulders, particularly when in the prone position on an operating table.

The surgery apparatus further includes a multipurpose holder device that is specifically designed for placement against the back of the patient's head, and has an arrangement of straps extending from a central portion. The straps and the central portion are preferably formed of an elastic or elastomeric, resilient material that permits stretching as needed. These strap segments are then connected to one strap that secures to an eye shield, another strap that secures to a bite block for placement in the patient's mouth and opposite left and right Y-shaped straps that assist for securing the endotracheal tube to the patient's mouth with the use of an adhesive fastening strip. The straps that extend to the eye shield, bite block, as well as the Y-shaped straps are provided with hook and loop fastening components. In particular, the opposite left and right Y-shaped straps are particularly useful on a patient that has a mustache and/or other facial hair. In this instance, one of the Y-shaped straps has a smooth surface for placement against the patient's face (i.e., overlying the patient's mustache or other facial hair above and below the lips). The top side of this first Y-shaped strap has one component of a hook and loop fastener which is intended for mating, releasable attachment to the corresponding component of a hook and loop fastener that is provided on the bottom side of the opposite Y-shaped strap. This allows the second Y-shaped strap to overlap and be secured to the first Y-shaped strap above and below the patient's lips. The top side of the second Y-shaped strap is also provided with one component of a hook and loop fastener that allows for releasable attachment of the adhesive fastening strip. The adhesive fastening strip includes opposite end portions having the corresponding component of a hook and loop fastener for attachment to the top surface of the second Y-shaped strap, while a center portion of the fastening strip has an adhesive material that is intended to be wrapped around and secured to the endotracheal tube exiting the patient's mouth. This fastening strip, once adhered around the endotracheal tube, can be attached to the second Y-shaped strap using the hook and loop fasteners, thereby effectively securing the endotracheal tube to the patient's mouth to prevent accidental dislodgement or movement during surgery.

BRIEF DESCRIPTION OF THE DRAWINGS

For a fuller understanding of the nature of the present invention, reference should be had to the following detailed description taken in connection with the accompanying drawings in which:

FIG. 5 is a top perspective view of a multipurpose holder device of the present invention including a central main body and a plurality of securing straps extending therefrom including opposite left and right Y-shaped endotracheal tube securing straps, an eye shield holder strap and a bite guard holder strap;

FIG. 6 is a top perspective view of an endotracheal tube fastening strip for use in conjunction with the Y-shaped securing straps in FIG. 5 for securing an endotracheal tube exiting a patient's mouth during surgery;

FIG. 7 is an isolated perspective view of an example of an eye shield attached to an end of one of the securing straps of the multipurpose holder device shown in FIG. 5;

FIG. 8 is an isolated perspective view illustrating an example of a bite guard attached to an end of a securing strap extending from the multipurpose holder device of FIG. 5;

Like reference numerals refer to like parts throughout the several views of the drawings.

DETAILED DESCRIPTION OF THE PREFERRED EMBODIMENT

Figure 1:
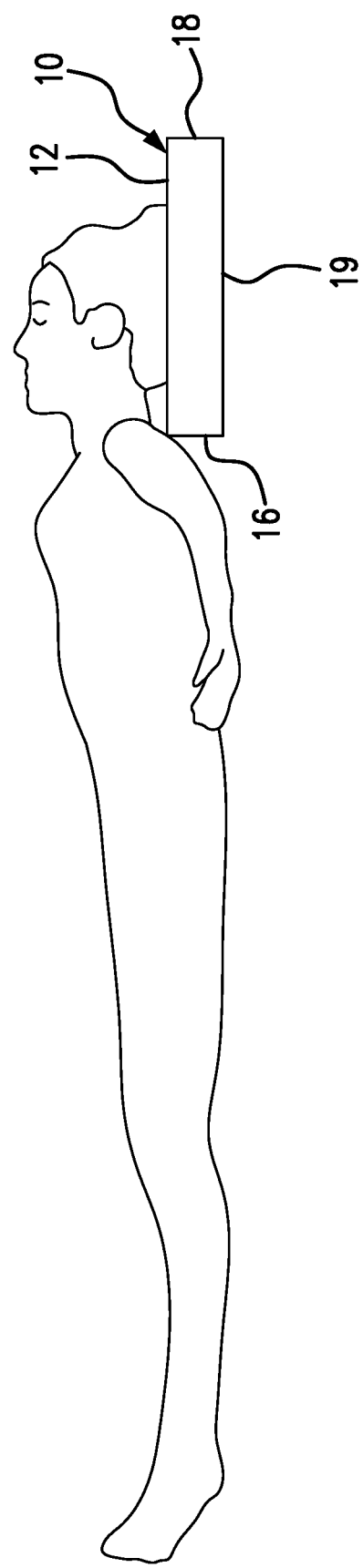
FIG. 1 is a side elevational view illustrating a patient lying in the supine position with the patient's head resting on the surgery pillow of the present invention.
Figure 2:
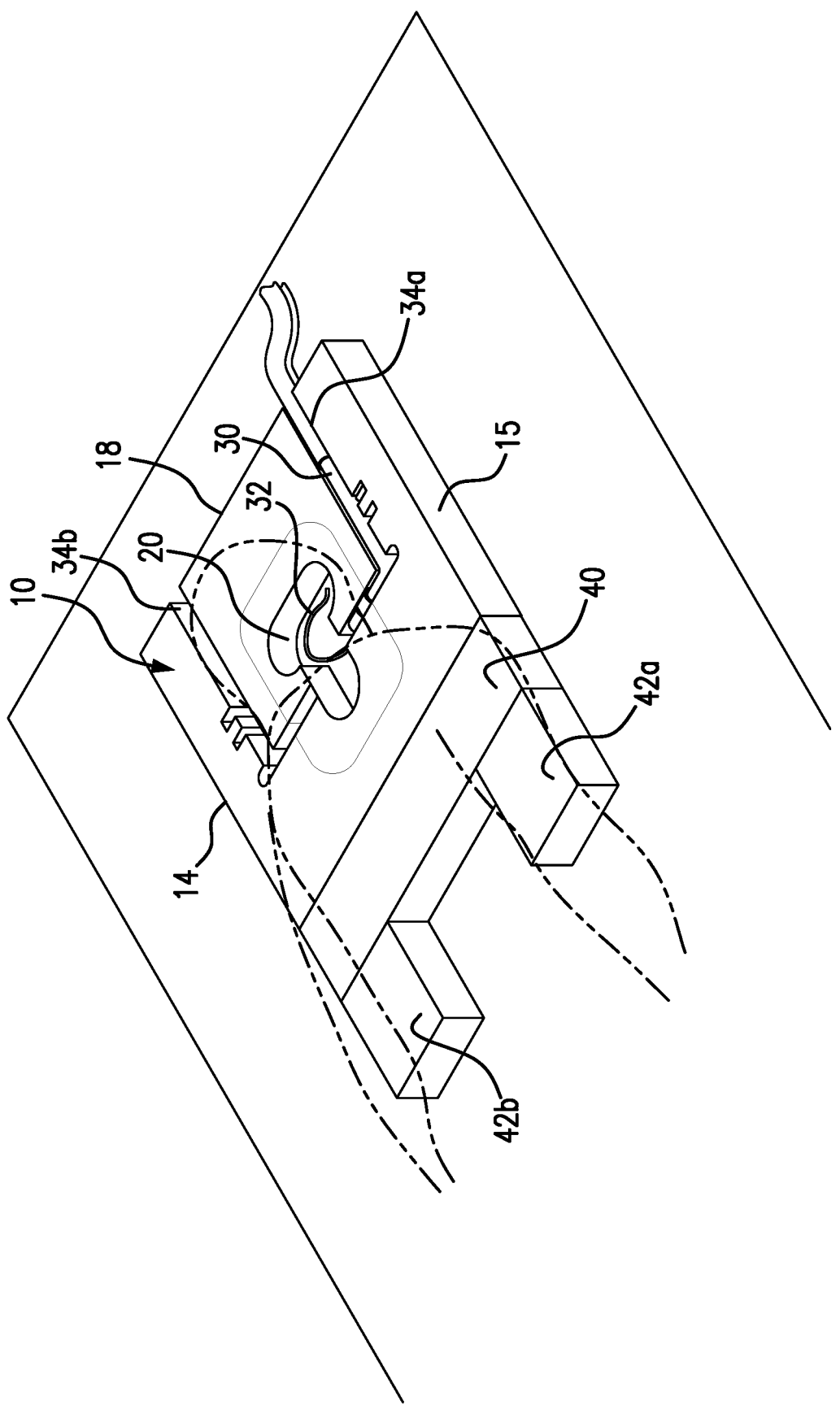
FIG. 2 is a top perspective view showing the surgery pillow of the present invention with a patient lying in the prone position with the patient's head face down within a cutout area of the pillow, and a chest support and shoulder supports attached to the pillow, and wherein an outline of the patient is illustrated in broken lines.
Figure 9:
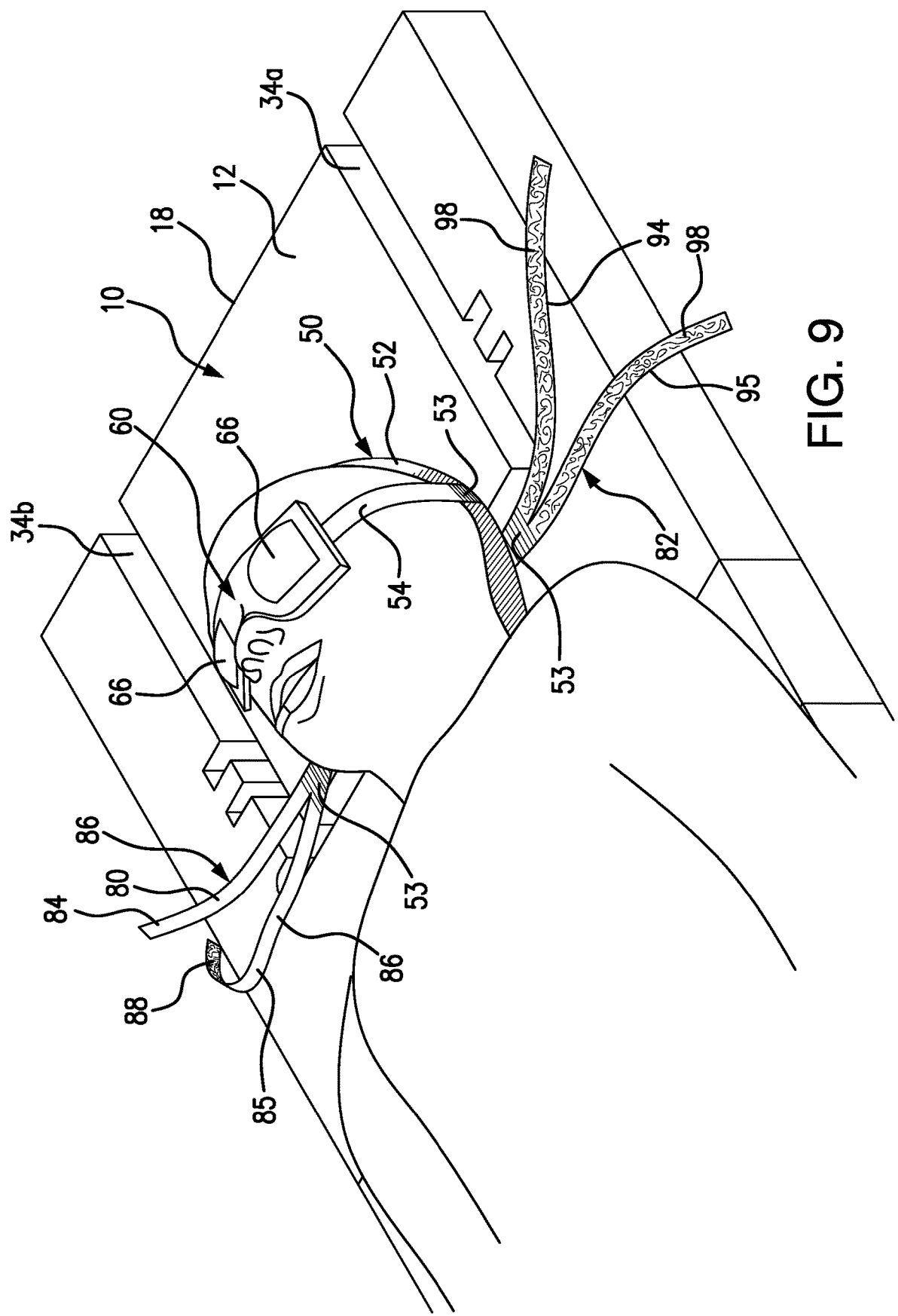
FIG. 9 is a top perspective view showing a surgery patient lying in a supine position on the surgery pillow of the present invention and further illustrating the multipurpose holder device positioned behind the patient's head.

Referring to the several views of the drawings, the surgery apparatus of the present invention is shown. The surgery apparatus includes a resilient foam pillow 10 for supporting a patient's head while on an operating table for surgery, as illustrated in FIGS. 1, 2 and 9. The surgery apparatus further includes a multipurpose holder device 50 that is designed for placement against the back of the patient's head allowing ready availability and ease of access and placement of a variety of items on the patient in preparation for surgery including an eye shield, bite guard and endotracheal tube securing mechanism, as shown in FIGS. 5-10.

The foam surgery pillow 10 has a top side 12, opposite side edges 14, 15, a lower edge 16 and an upper edge 18. A bottom side 19 of the pillow 10 lies against the operating table during surgery. The top side 12 of the pillow is provided with a central cutout open area 20 that is specifically shaped, sized and positioned for accommodating the surgery patient's face when in the prone position, as seen in FIG. 2. In particular, the central cutout area 20 allows the patient to lie face down while not interfering or applying any pressure to the patient's eyes, nose or mouth. This central cutout area 20 further allows for exit of the endotracheal tube 32 of the breathing tube system 30 during surgery. The top side 12 of the pillow 10 is further provided with left and right channels 34a and 34b that are specifically sized, shaped and positioned to receive a typical breathing tube system 30, as illustrated in FIG. 2. The left and right channels 34a, 34b both extend from the upper edge 18 of the pillow and are generally L-shaped, turning inwardly and communicating with the central cutout area 20. This allows the endotracheal tube 32 to exit the patient's mouth, while in the prone position, and to connect with the breathing tube system 30 which is seated within one of the channels, as illustrated in FIG. 2, without interference. Depending on the positioning of the patient and the preference of the anesthesiologist, the breathing tube system may be fitted in either the left channel 34a or the right channel 34b of the surgery pillow.

The resilient foam surgery pillow 10 further includes removably attachable supports for placement under the patient during surgery. In particular, a chest support 40 is provided that extends generally the full width of the pillow and is adapted for removable attachment to the lower edge 16 of the pillow by any well-known releasable attachment mechanism, such as hook and loop fasteners. The removably attachable supports further include resilient foam shoulder supports 42a, 42b that may be used with or without the foam chest support 40. FIG. 2 illustrates the left and right shoulder supports 42a, 42b used in conjunction with the chest support 40, wherein the shoulder supports 42a, 42b are releasably attachable to opposite end portions of the chest support 40 for supporting the patient's shoulder and upper arms while in the prone position during surgery. In some instances, the chest support 40 may not be needed, but it may still be desirable to use the shoulder supports 42a, 42b. In this instance, the left and right shoulder supports 42a, 42b are releasably attachable to the lower edge 16 of the pillow 10. When used with the chest support 40, the left and right shoulder supports 42a, 42b are releasably attachable to a lower edge of the chest support 40, in the same manner using any well-known releasable fastening mechanism, such as hook and loop fasteners.

Figure 3:
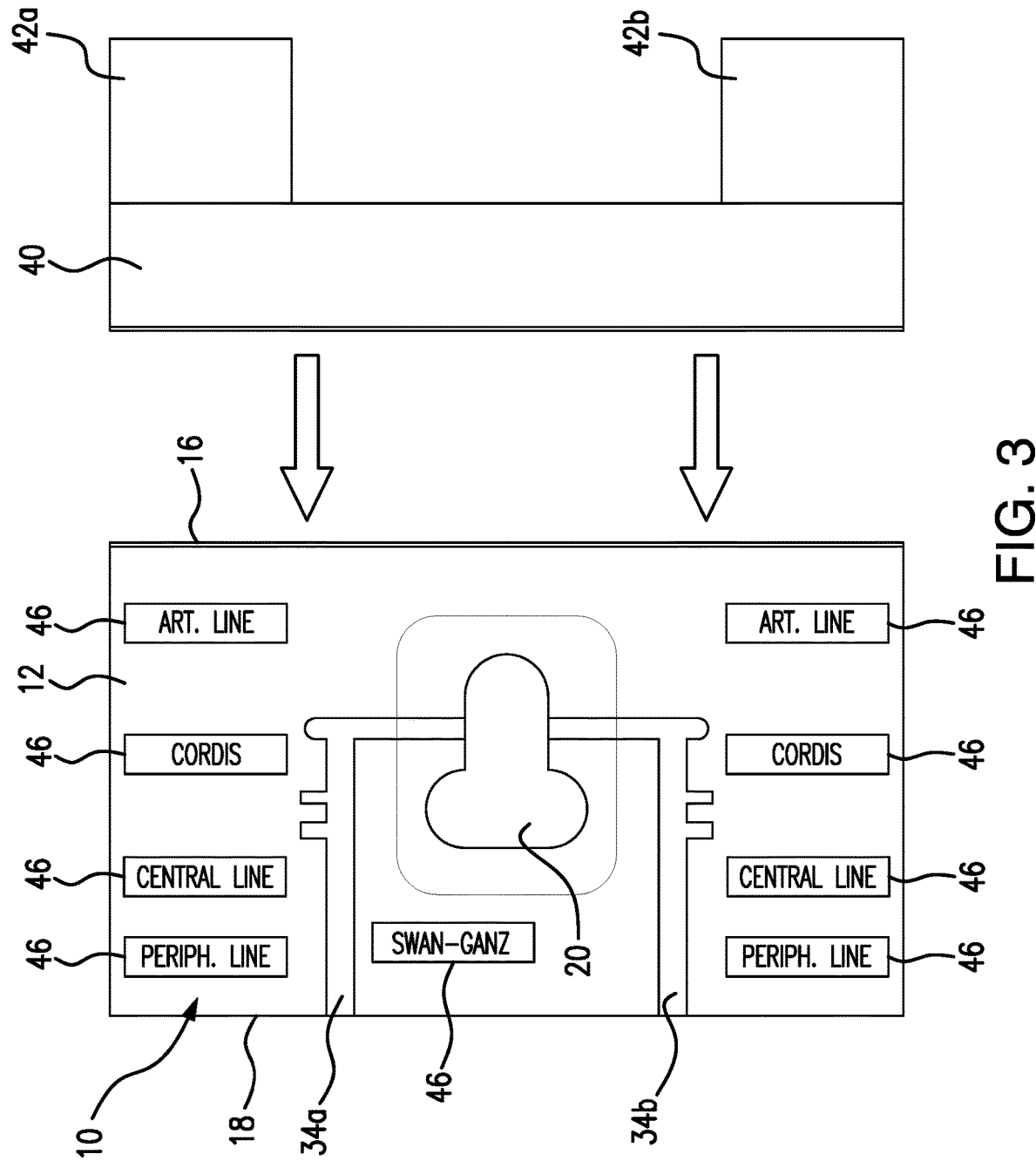
FIG. 3 is a top plan view illustrating the surgery pillow of the present invention, and further illustrating a chest support and shoulder supports removably attached to a bottom edge of the surgery pillow, as indicated by the arrows.
Figure 4:
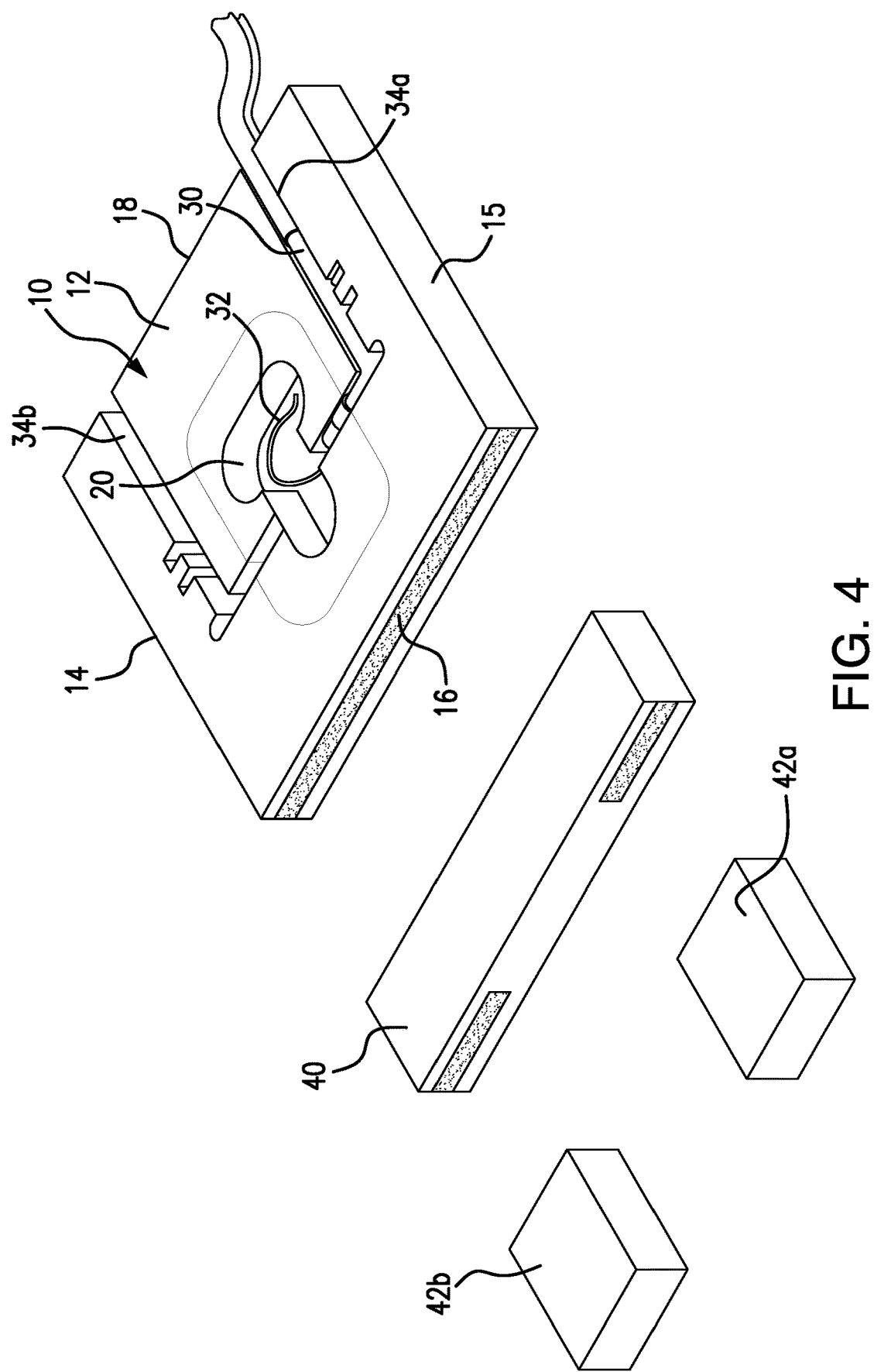
FIG. 4 is an exploded top perspective view of the surgery pillow with the chest support and shoulder supports separated therefrom, and a breathing tube system fitted within a channel of the pillow.

Referring to FIG. 3, the top side 12 of the surgery pillow 10 may further be provided with labeled tabs 46 for holding various intravenous and arterial lines, tubes, catheters, monitoring cables, pressure transducers and other devices that are coming from or going to the patient on the operating table during surgery. Each of the labeled tabs 46 indicates the particular type of line, tube, cable, etc. that will be placed under that particular tab. In a preferred embodiment, each tab 46 is fixedly secured at one end to the top side of the pillow and may be provided with a releasable fastener at the other end of the tab for releasable attachment to the top surface of the pillow. The releasable fastener, such as a hook and loop fastener on both the top side of the pillow and the underside of the tab 46 allows the tab to be lifted from the top side of the pillow for placement of the specific line, cable, tube, etc. thereunder. This allows the anesthesiologist to organize these different intravenous and arterial lines, tubes, catheters, monitoring cables, pressure transducers, etc. so that each particular line, cable, tube, etc. can be quickly located and identified in preparation for surgery, during surgery and after surgery.

Figure 10:
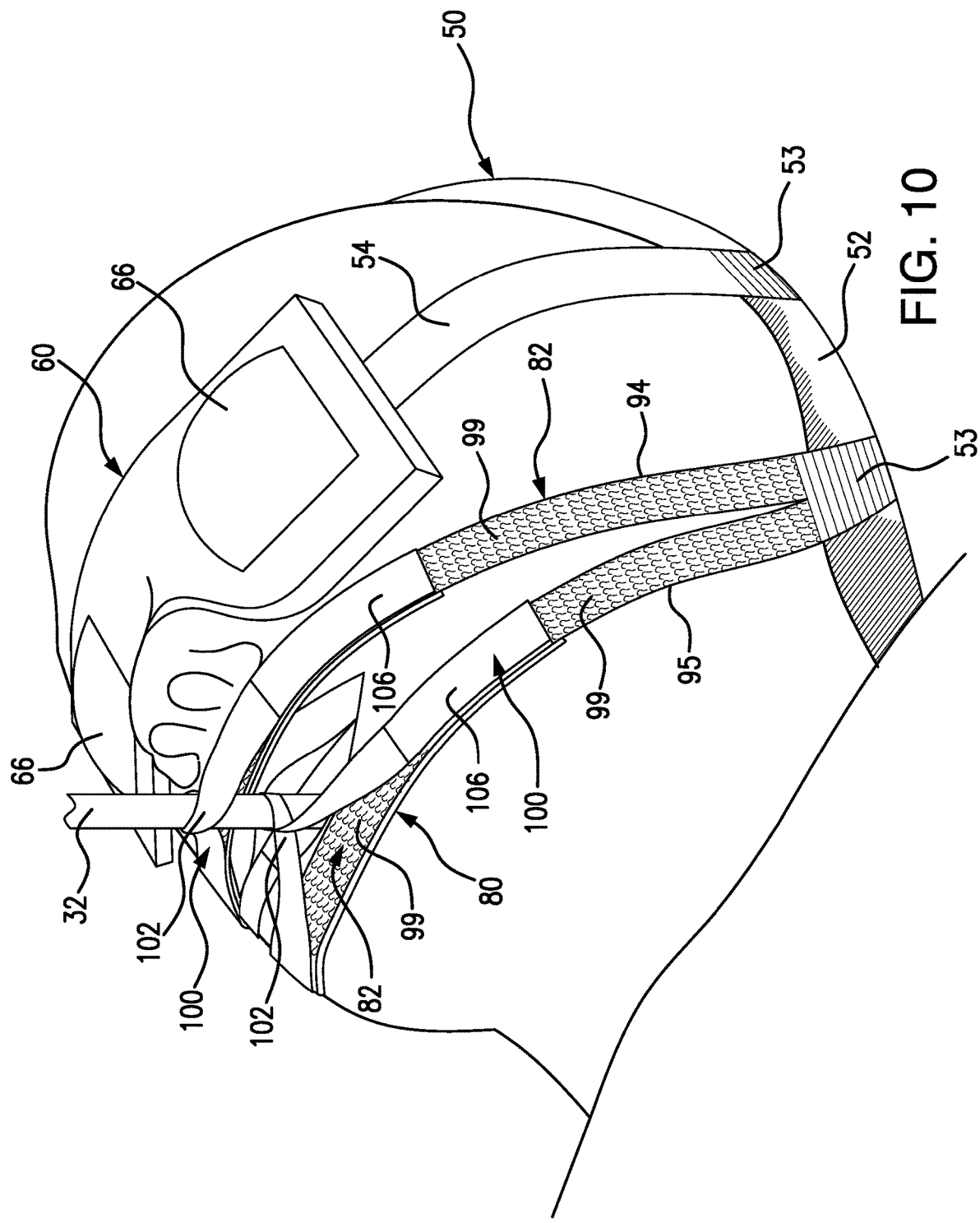
FIG. 10 is an isolated perspective view showing the surgery patient of FIG. 9 with the multipurpose holder device fully secured to hold the eye shield, bite guard and endotracheal tube secure for surgery.

Referring to FIGS. 5-10 the multipurpose holder device 50 is shown. The central main body 52 of the holder device may be formed in a general oval or egg shape, as seen in FIG. 5, and is intended for placement behind the surgery patient's head while on the operating table for surgery. The central oval shaped main body 52 may also be formed to be concave to fit more neatly against the back of the patient's head. Multiple securing straps extend from the opposite sides of the oval shaped main body 52 and include an elastomeric (i.e., stretchable and resilient) segment 53 to allow the straps to be pulled and stretched as need for proper fit to the patient as described further below. The central oval shaped main body 52 may also be made of the same elastomeric material. A first strap 54 extends from the main body 52 and has an eye shield 60 attached to an end thereof. The eye shield 60 is intended to be placed over the patient's eyes, as seen in FIGS. 9 and 10. Referring to FIG. 7, the eye shield 60 may include a peel away film 62 on the inner facing side to expose an adhesive 63 that allows the eye shield 60 to removably stick to the patient's skin when secured in place, as seen in FIGS. 9 and 10. The eye shield 60 further includes a foam or soft resilient body 64 that provides a comfortable engagement against the patient's facial skin surrounding the eyes but without touching the eyes. Protective lenses 66 on the eye shield 60 are preferably convex or bubble shaped to protrude away from the user's eyes to ensure that there is no contact of any part of the eye shield or any other objects with the patient's eyes during surgery. Another strap 56 extends from the opposite side of the oval shaped main body 52 and has a bite guard 70 secured to an end thereof. The bite guard 70 is placed within the patient's mouth when intubated with an endotracheal tube 32 to prevent the patient from biting down on the endotracheal tube 32, particularly when coming out of the anesthesia and beginning to wake up where it is necessary to remove the endotracheal tube 32 from the patient while the patient is still partially under anesthesia and not fully awake.

The multipurpose holder device 50 further includes Y-shaped straps 80, 82 for securing the endotracheal tube exiting the patient's mouth so that the endotracheal tube is not accidentally dislodged during surgery. Referring initially to FIG. 5, a first one of the Y-shaped straps 80 includes a pair of segments 84, 85 each having a smooth side 86 that is placed against the patient, above and below the lips, and a component 88 of a hook and loop fastener on the opposite side. The smooth side 86 of each of the two segments is placed against the patient's face, and particularly above the upper lip and below the lower lip, as seen in FIG. 10. The smooth surface 86 of the two strap segments 84, 85 prevents irritation or injury to the user's skin. It should be noted that the two Y-shaped straps on the multipurpose holder device are particularly useful for use on patients having a mustache and/or other facial hair. In this instance, the smooth surface 86 of the one segment 84 of the first Y-strap 80 is placed over the mustache and the smooth surface 86 on the other strap segment 85 of the first Y-strap 80 lies against the skin or other facial hair below the lower lip of the patient. At this point, the one component 88 of the hook and loop fasteners on the opposite sides of the segments 84, 85 of the first Y-shaped strap 80 are facing up and are positioned for corresponding releasable attachment of the opposite component 98 of the hook and loop fastener on the opposing segments 95, 95 of the second Y-shaped strap 82, as seen in FIG. 10. In this positioning, as seen in FIG. 10, the two Y-shaped securing straps 80, 82 are fitted and attached to one another, extending across the face and above the upper lip and below the lower lip. Thereafter, one or two fastening strips 100 can be attached to one or both of the Y-shaped securing straps 80, 82. The fastening strip 100, as seen in FIGS. 6 and 10, has a central portion 102 provided with an adhesive surface that is initially protected by a peel away film 103. In use, the peel away film 103 is removed to expose the adhesive surface 104 that is then wrapped around the endotracheal tube 32 exiting the patient's mouth, as seen in FIG. 10. Thereafter, the opposite ends 106, 108 of the securing strap segments, each having a component 110 of hook and loop fastener material thereon, are secured to the upper facing side of the second Y-shaped securing strap 82, for releasable attachment to the opposing component 99 of the hook and loop fastener on the top surface of the second Y-shaped securing strap 82. In this manner, the endotracheal tube 32 exiting the surgery patient's mouth is secured in place, as seen in FIG. 10, and will not be accidentally moved or dislodged during surgery.

Since many modifications, variations and changes in detail can be made to the described embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A surgery apparatus comprising:
    a resilient foam pillow for supporting a patient's head while on an operating table for surgery, the pillow including a top side, an upper edge and a lower edge and the top side including a central cavity for placement of a patient's face when in the prone position on the operating table, and the top side of the pillow further including at least one recessed channel formed therein and extending from the upper edge to the central cavity for receiving a breathing tube system therein;
    a multipurpose holder device including a central portion and a plurality of straps extending from the central portion including a first Y-shaped strap extending from one side of the central portion and a second Y-shaped strap extending from an opposite side of the central portion, a third strap extending from one side of the central portion and a fourth strap extending from the opposite side of the central portion;
    the first Y-shaped strap including a main strap portion connected to the central portion of the multipurpose holder device at one end and a pair of segments extending from an opposite second end of the main strap portion, and each of the pair of segments having a smooth bottom inner facing side for placement against the patient's face, above and below the lips, and each of the pair of segments further including a top, outer facing side with a component of a first hook and loop releasable fastener on the top, outer facing side;
    the second Y-shaped strap including a main strap portion connected to the central portion of the multipurpose holder device at a first end and a pair of segments extending from an opposite second end of the main strap portion, and the pair of segments of the second Y-shaped strap being structured and disposed for overlapping attachment to the pair of segments of the first Y-shaped strap, and the pair of segments of the second Y-shaped strap having a component of a second hook and loop releasable fastener on bottom, inner facing sides for releasable attachment to the component of the first hook and loop releasable fastener on the top, outer facing sides of the pair of segments of the first Y-shaped strap, and the pair of segments of the second Y-shaped strap further including top, outer facing sides with a component of a third hook and loop releasable fastener on the top, outer facing sides; and
    at least one fastening strip for securing an endotracheal tube exiting the patient's mouth while on the operating table for surgery, and the fastening strip including opposite end portions having a component of a fourth hook and loop releasable fastener for releasable attachment to the component of the third hook and loop releasable fastener on the top, outer facing sides of the pair of segments of the second Y-shaped strap, and the fastening strip further including a central portion having an adhesive surface for attachment to the endotracheal tube.

2. The surgery apparatus as recited in claim 1 further including a chest support formed of a resilient foam material and removably positionable adjacent to the lower edge of the pillow.

3. The surgery apparatus as recited in claim 2 further including left and right shoulder support pads formed of a resilient foam material and removably and selectively positionable adjacent to the lower edge of the pillow or adjacent to the chest support.

4. The surgery apparatus as recited in claim 1 further comprising:
    a plurality of labeled tabs on the top side of the pillow for holding various intravenous and arterial lines, tubes, catheters, monitoring cables, pressure transducers and other devices that are coming from or going to the patient on the operating table during surgery.

5. The surgery apparatus as recited in claim 1 wherein the multipurpose holder device further comprises:
    an eye shield attached to a distal end of the third strap.

6. The surgery apparatus as recited in claim 1 wherein the multipurpose holder device further includes a bite guard attached to a distal end of the fourth strap.

* * * * *